United States Patent

Wu

[11] Patent Number: 5,951,491
[45] Date of Patent: Sep. 14, 1999

[54] SYRINGE FOR DRAWING BLOOD

[76] Inventor: Tan Wu, No. 19, Yong Din Road. Er Ruen Hsiang, Yuen Lin Hsien, Taiwan

[21] Appl. No.: 09/006,533

[22] Filed: Jan. 13, 1998

[51] Int. Cl.[6] .................................................. A61B 5/00
[52] U.S. Cl. ............................................................ 600/576
[58] Field of Search .................................. 600/576–578, 600/583; 604/190

[56] References Cited

U.S. PATENT DOCUMENTS

| | | | |
|---|---|---|---|
| 4,378,812 | 4/1983 | Sarstedt | 128/765 |
| 4,418,703 | 12/1983 | Hoch et al. | 600/576 |
| 4,459,997 | 7/1984 | Sarstedt | 128/764 |
| 4,732,162 | 3/1988 | Martell | 128/765 |
| 5,074,312 | 12/1991 | Sarstedt | 128/764 |
| 5,095,914 | 3/1992 | Sarstedt | 128/765 |

*Primary Examiner*—Max Hindenburg

[57] ABSTRACT

A syringe includes a needle secured to one end of a barrel by a coupler which has a check valve engaged in the barrel. A housing is secured to the barrel. The check valve may prevent the blood from flowing through the coupler when the housing is disengaged from the barrel. The coupler includes a tip. The check valve includes a sleeve engaged on the tip of the coupler and having a resilience for clamping the tip and for blocking the coupler. A piston is slidably engaged in the housing for vacuuming the housing and for drawing blood into the housing via the needle and the coupler.

1 Claim, 5 Drawing Sheets

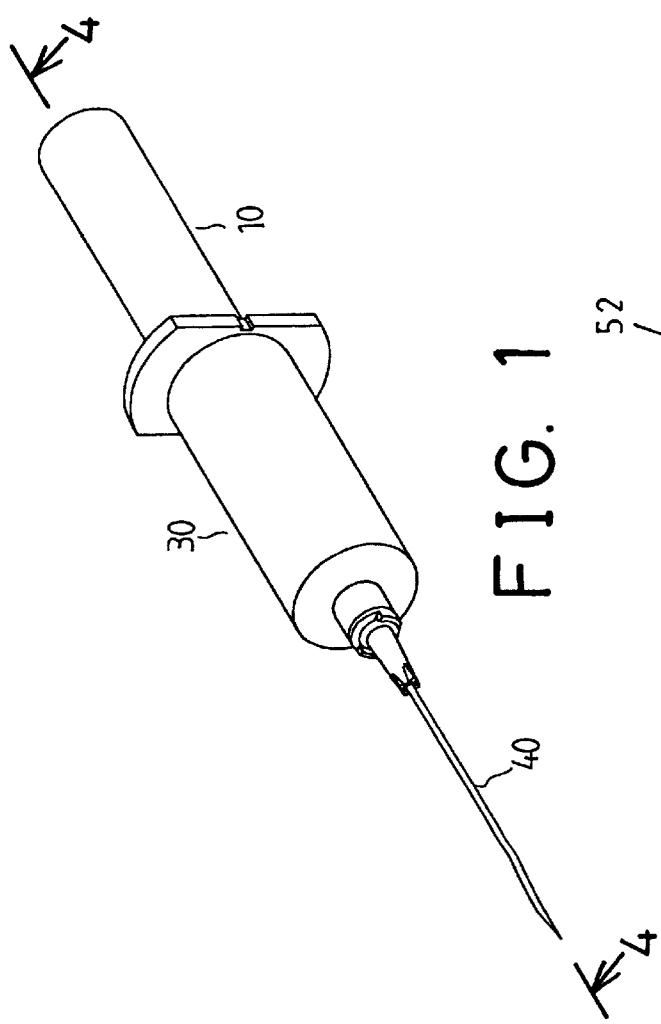
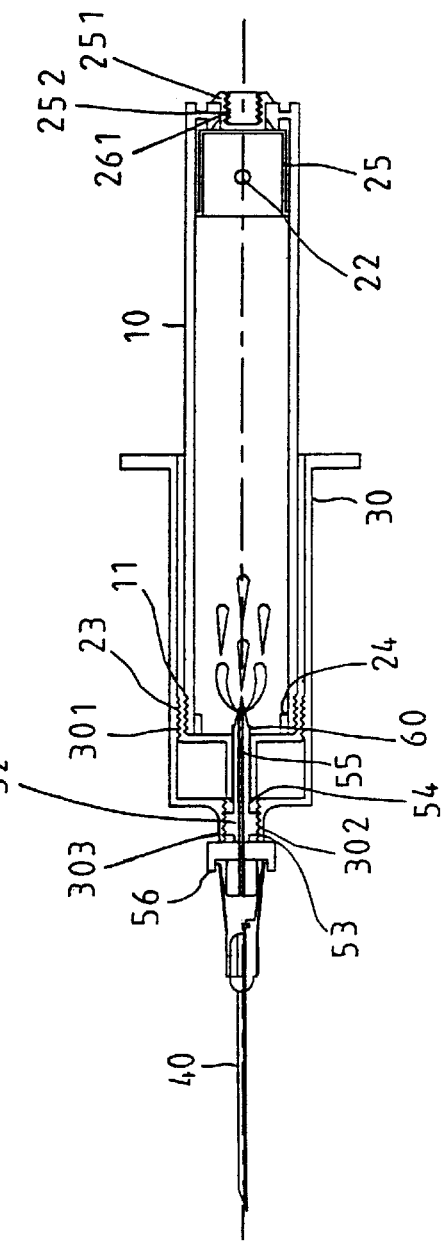

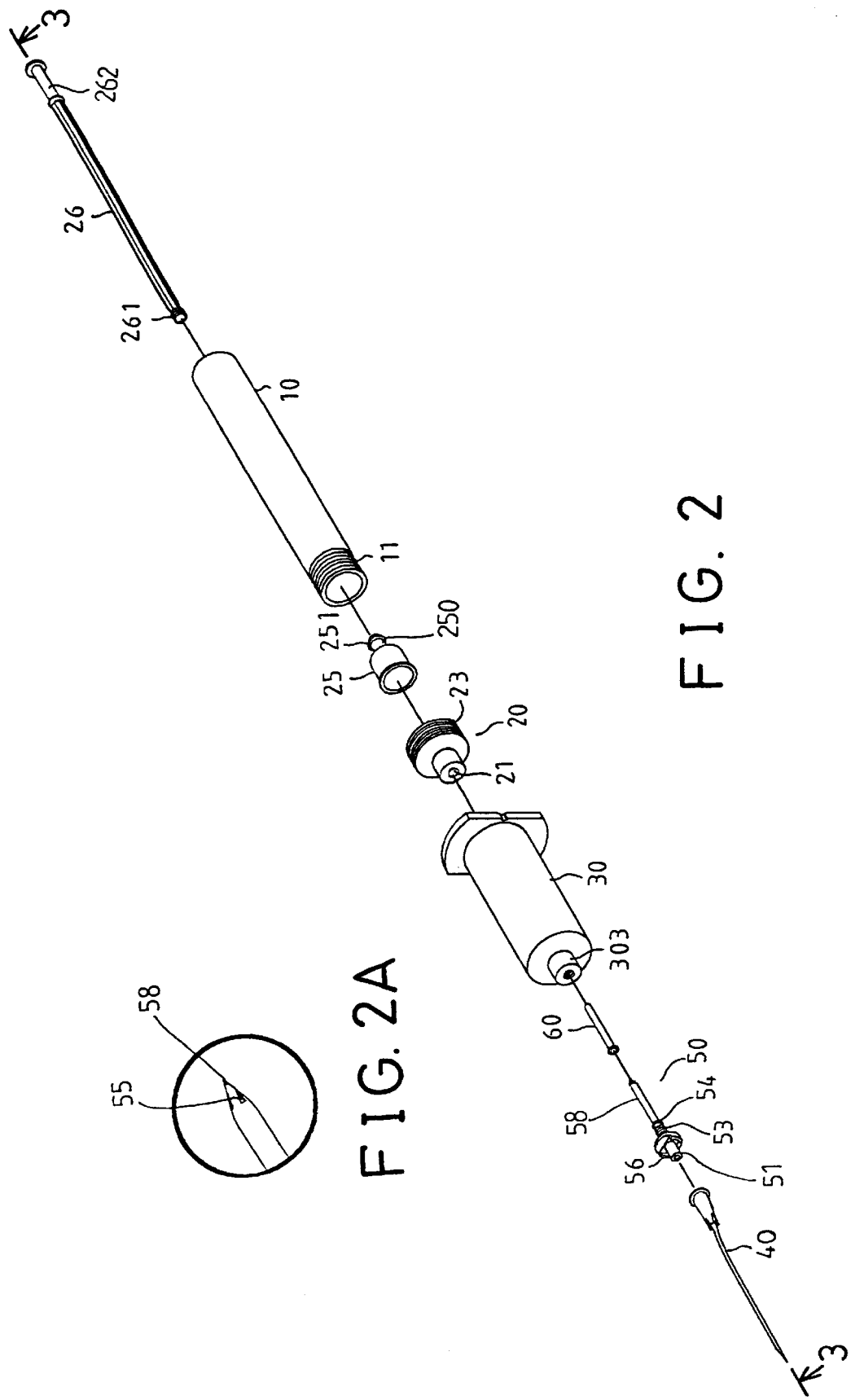

ion this page.

SYRINGE FOR DRAWING BLOOD

BACKGROUND OF THE INVENTION

1. Field of the Invention

The present invention relates to a syringe, and more particularly to a syringe for drawing blood.

2. Description of the Prior Art

Typical syringes comprise a cylindrical housing and a piston slidably engaged in the cylindrical housing and movable in the cylindrical housing for forcing the medicine in the syringe into the human body or for drawing the blood into the syringe from the human body. However, in some cases, the volume of the syringe is not good enough for receiving the blood of required amount, such that the needle has to be removed from the human body and the other needle of the other syringe is required to be engaged into the human body again for drawing the blood.

The present invention has arisen to mitigate and/or obviate the afore-described disadvantages of the conventional syringes.

SUMMARY OF THE INVENTION

The primary objective of the present invention is to provide a syringe including one or more housings for engaging with a single needle and for allowing the blood to be drawn into the housings without disengaging the needle from the human body.

In accordance with one aspect of the invention, there is provided a syringe comprising a barrel including a first end having a port, a coupler secured to the port, a needle secured to the first end of the coupler, a housing secured to the barrel, and a check valve provided in the second end of the coupler for preventing the blood from flowing through the coupler when the housing is disengaged from the barrel.

The coupler includes a through hole and a tip, the check valve includes a sleeve engaged on the tip of the coupler and having a resilience for clamping the tip and for blocking the through hole of the coupler.

The housing includes a cap secured to the housing and having a mouth for engaging with the tip of the coupler. The cap includes a ball engaged in the mouth for engaging with the tip and for allowing the tip to disengage the ball from the mouth when the mouth of the cap is engaged with the tip of the coupler.

A piston is slidably engaged in the housing for vacuuming the housing. A rod is secured to the piston for moving the piston along the housing and for drawing the blood into the housing. The housing includes a second end and further includes a retaining means for securing the piston to the second end of the housing. The protrusion of the piston includes a latch for engaging with the second end of the housing and for securing the piston to the second end of the housing.

Further objectives and advantages of the present invention will become apparent from a careful reading of a detailed description provided hereinbelow, with appropriate reference to accompanying drawings.

BRIEF DESCRIPTION OF THE DRAWINGS

FIG. 1 is a perspective view of a syringe in accordance with the present invention;

FIG. 2 is an exploded view of the syringe;

FIG. 2A is an enlarged partial perspective view showing the tip of the needle;

FIG. 4 is a cross sectional view taken along lines 4—4 of FIG. 1; and

DETAILED DESCRIPTION OF THE PREFERRED EMBODIMENT

Figure 3:
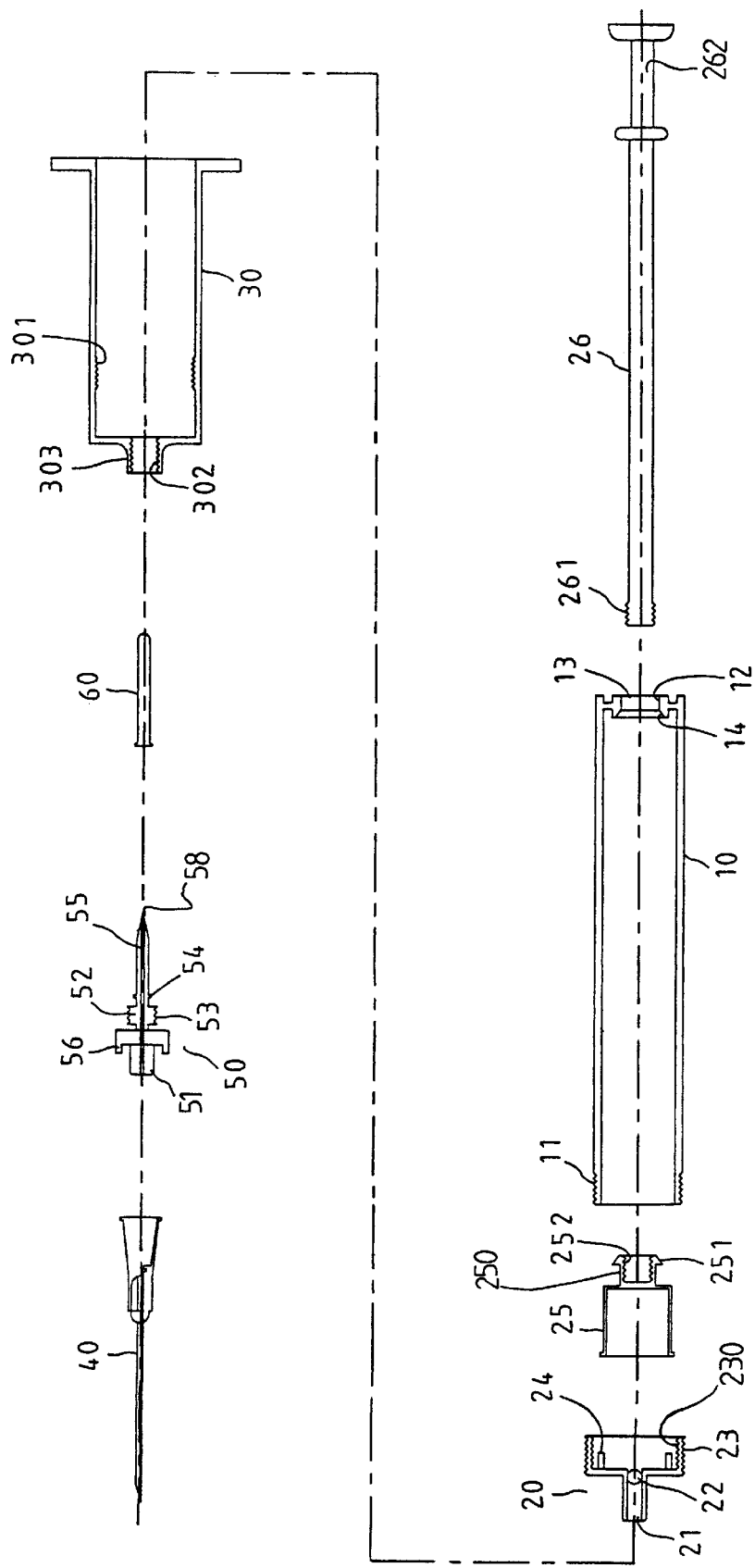
FIG. 3 is a cross sectional view taken along lines 3—3 of FIG. 2.

Referring to the drawings, and initially to FIGS. 1–4, a syringe in accordance with the present invention comprises one or more housings 10 each including an open end for receiving blood and an outer thread 11 formed on the outer peripheral portion of the open end. The housing 10 includes an annular flange 12 formed in the other end and an opening 13 formed in the annular flange 12 and an annular tapered surface 14 formed in the annular flange 12 and located in the housing 10. A cap 20 includes a mouth 21 and includes an outer thread 23 and an inner thread 230 which is engaged with the outer thread 11 of the housing 10 for allowing the cap 20 to be secured to the housing 10. The cap 20 includes one or more stops 24 for engaging with the housing 10 and for solidly retaining the housing 10 in place. A ball 22 is engaged in the mouth 21 of the cap 20 for blocking the mouth 21 of the cap 20.

A piston 25 is slidably engaged in the housing 10 and includes a protrusion 250 having a latch 251 and an inner thread 252. The latch 251 includes an annular tapered surface for engaging with the tapered surface 14 of the annular flange 12 and for allowing the protrusion 250 of the piston 25 to be engaged through the opening 13 and engaged with the annular flange 12 for securing the piston 25 to the annular flange 12 (FIGS. 4–7). A rod 26 is slidably engaged through the opening 13 of the housing 10 and includes an outer thread 261 for threadedly engaging with the inner thread 252 of the piston 25 and for allowing the rod 26 to be secured to the piston 25 and for allowing the piston 25 to be moved along the housing 10 by the rod 26. The rod 26 includes a handle 262 provided on the other end for actuating the rod 26 and the piston 25. After the protrusion 250 of the piston 25 is secured to the annular flange 12 of the housing 10, the interior of the housing 10 may thus be vacuumed by the piston 25. At this moment, the rod 26 may be bent relative to the housing 10 for leaving the end portion of the rod 26 in the protrusion 250 and for removing the rod 26 from the housing 10.

A barrel 30 includes an inner thread 301 formed in the front and inner peripheral portion and includes a port 303 extended outward from the front portion and having an inner thread 302. The inner thread 301 of the barrel 30 is provided for threadedly engaging with the outer thread 23 of the cap 20 (FIG. 4) and for allowing the housing 10 to be solidly secured to the barrel 30. A coupler 50 includes an annular bulge 52 formed in the middle portion and having an outer thread 53 for threadedly engaging with the inner thread 302 of the barrel 30 and for allowing the coupler 50 to be secured to the barrel 30. The coupler 50 includes a projection 51 and annular rib or one or more ribs 56 for engaging with a needle 40 and for allowing the needle 40 to be secured to the coupler 50. The coupler 50 includes a through hole 55 and includes a tip 58 extended inward of the barrel 30 and includes an annular rib 54. A condom or rubber sleeve 60 is engaged on the tip 58 of the coupler 50 and includes one end for engaging with the annular rib 54 and for allowing the rubber sleeve 60 to be secured to the coupler 50. The rubber sleeve 60 includes a suitable resilience for clamping the tip 58 of the coupler 50 and for blocking the through hole 55 of the coupler 50 even when the rubber sleeve 60 is broken by the tip 58 of the coupler 50. The rubber sleeve 60 for blocking the through hole 55 forms a check valve. The coupler 50 is preferably made of transparent material such that the user may view the flowing of the blood through the through hole 55 of the coupler 50.

Figure 7:
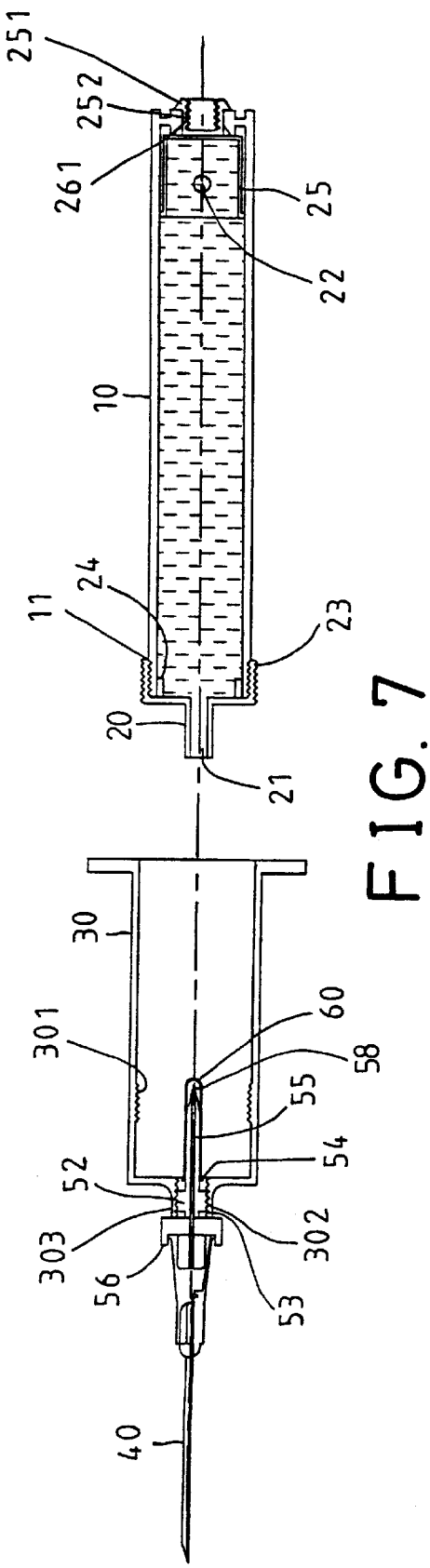
Figure 6:
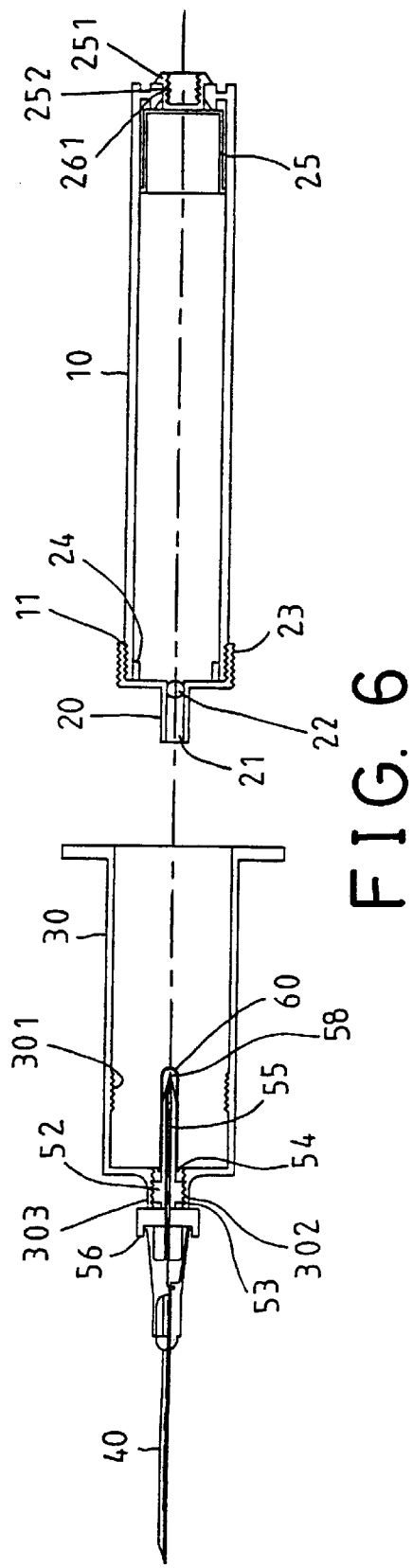

In operation, as shown in FIG. 6, the housing 10 may first be vacuumed by the piston 25 and the needle 40 is engaged into the human body whose blood is required to be drawn into the housing 10. The mouth 21 of the cap 20 is then engaged with the tip 58 of the coupler 50. The ball 22 may be forced to move inward of the housing 10 by the tip 58 of the coupler 50. In addition, the sleeve 60 may be broken by the tip 58 when the tip 58 is engaged with the ball 22. It is preferable that the ball 22 is disengaged from the mouth 21 after the outer thread 23 is threadedly engaged with the inner thread 301 of the barrel 30. When the sleeve 60 is broken, the blood may thus be drawn into the housing 10 automatically via the needle 40 and the coupler 50 due to the vacuumed interior of the housing 10. As shown in FIG. 7, when the housing 10 which is filled with blood is removed from the barrel 30, the sleeve 60 may also clamp the tip 58 of the coupler 50 for blocking the through hole 55 of the coupler 50 and for preventing the blood from flowing out of the coupler 50 when the housing 10 is disengaged from the barrel 30. Another housing 10 may thus be engaged with the coupler 50 for drawing the blood into another housing 10 without disengaging the needle 40 from the human body.

Figure 5:
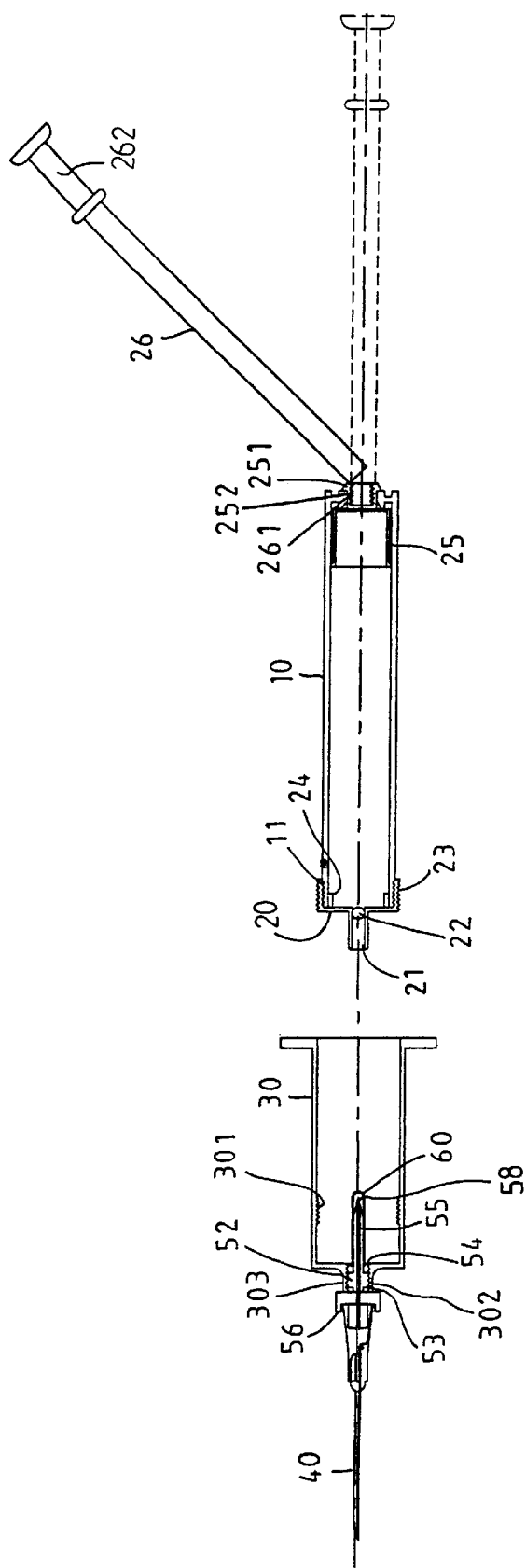
FIGS. 5, 6 and 7 are cross sectional views illustrating the operation of the syringe.

Alternatively, as shown in dotted lines of FIG. 5, the piston 25 may also be pulled by the rod 26 manually after the mouth 21 is secured to the coupler 50 for drawing the blood into the housing 10 manually. The sleeve 60 may also be arranged to be broken by the tip 58 when the coupler 50 is secured to the barrel 30. Or, the sleeve 60 may first be broken before secured onto the coupler 50 and may still clamp the tip 58 of the coupler 50 for blocking the through hole 55. The housing 10 may also be vacuumed by a facility without slidably moving the piston 25 from one end of the housing 10 to the other end.

Accordingly, the syringe in accordance with the present invention includes one or more housings for engaging with a single needle and for allowing the blood to be drawn into the housings without disengaging the needle from the human body.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A syringe comprising:

a barrel including a first end having a port, a coupler secured to said port of said barrel and including a first end and a second end, said coupler including a through hole and including a tip formed in said second end thereof, a needle secured to said first end of said coupler, a check valve including a sleeve engaged on said tip of said coupler and having a resilience for clamping said tip and for blocking said through hole of said coupler, and a housing including a first end secured to said barrel and including a cap secured to said first end of said housing and having a mouth for engaging with said tip of said coupler, said cap including a ball engaged in said mouth for enclosing said first end of said housing and for engaging with said tip of said coupler and for allowing said tip to disengage said ball from said mouth when said mouth of said cap is engaged with said tip of said coupler, said housing including a second end, a piston slidably engaged in said housing for vacuuming said housing and for drawing blood into said housing via said needle and said coupler, said piston including a protrusion having a latch for engaging with said second end of said housing and for securing said piston to said second end of said housing, means for moving said piston along said housing for vacuuming said housing, said moving means including a rod secured to said protrusion of said piston for moving said piston along said housing and for drawing the blood into said housing, said check valve being provided for preventing the blood from flowing through said coupler when said housing is disengaged from said barrel.

* * * * *